US009980862B2

(12) United States Patent
Arefieg

(10) Patent No.: US 9,980,862 B2
(45) Date of Patent: *May 29, 2018

(54) ADHESIVE BANDAGE DISPENSING ARRANGEMENTS

(71) Applicant: Thuban, Inc., Ridgefield, CT (US)

(72) Inventor: Rana J. Arefieg, Ridgefield, CT (US)

(73) Assignee: Thuban, Inc., Ridgefield, CT (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/466,609

(22) Filed: Aug. 22, 2014

(65) Prior Publication Data

US 2014/0361056 A1 Dec. 11, 2014

Related U.S. Application Data

(63) Continuation of application No. 13/068,723, filed on May 18, 2011, now Pat. No. 8,851,284.

(51) Int. Cl.
*A61F 13/00* (2006.01)
*A61F 15/00* (2006.01)
(Continued)

(52) U.S. Cl.
CPC .............. *A61F 15/002* (2013.01); *A45F 3/00* (2013.01); *A61F 13/00076* (2013.01);
(Continued)

(58) Field of Classification Search
CPC .................. A45F 3/00; A45F 2003/003; A45F 2003/006; A61F 13/00076; A61F 15/002; A61F 15/02; B26F 3/02; B65D 27/00; B65D 83/0805; B65D 83/0847; B65D 85/671; Y10T 225/23; Y10T 225/232; Y10T 225/237; Y10T 225/238; Y10T 225/241; Y10T 225/246

USPC ............ 225/32, 34, 38, 39, 42, 46; 206/390, 206/394, 400, 401, 409, 411, 440, 441, 206/460, 464, 494, 820; 221/25, 26, 70; 242/590, 594.3, 594.5, 598.6; 602/41–43, 602/52, 54, 57–59, 900

See application file for complete search history.

(56) References Cited

U.S. PATENT DOCUMENTS 3,520,403 A 7/1970 Moshel
3,530,494 A 9/1970 Baratta
(Continued)

OTHER PUBLICATIONS

European Search Report in EP appln. No. 12785293.7 (PCT/US2012/37982), dated Oct. 17, 2014.
(Continued)

*Primary Examiner* — Clark F Dexter
(74) *Attorney, Agent, or Firm* — David M. Quinlan, P.C.

(57) ABSTRACT

A bandage strip includes a plurality of flat adhesive bandage packages of conventional configuration, having sealed therein an adhesive bandage with a pad and an adhesive substrate for adhering to as patient and holding the pad in place on the patient's skin. The packages are adhered to an elongated substrate in end-to-end, spaced relation to form a flat, elongated bandage strip, with perforations in the substrate between the packages. A user can dispense a length of substrate, sever it at the perforations, and remove the bandage from the substrate for use in the conventional manner. A bandage dispensing device is attachable to the wrist of a user for convenient dispensing of bandages from a strip of individually packaged bandages.

14 Claims, 5 Drawing Sheets

(51) Int. Cl.
*B26D 3/02* (2006.01)
*B65D 83/08* (2006.01)
*B65D 85/671* (2006.01)
*A45F 3/00* (2006.01)
*A61F 15/02* (2006.01)
*B65D 27/00* (2006.01)

(52) U.S. Cl.
CPC ............... *A61F 15/02* (2013.01); *B26D 3/02* (2013.01); *B65D 27/00* (2013.01); *B65D 83/0805* (2013.01); *B65D 83/0847* (2013.01); *B65D 85/671* (2013.01); *A45F 2003/003* (2013.01); *A45F 2003/006* (2013.01); *Y10T 225/23* (2015.04); *Y10T 225/232* (2015.04); *Y10T 225/241* (2015.04)

(56) References Cited

U.S. PATENT DOCUMENTS

| | | | |
|---|---|---|---|
| 3,826,407 A | 7/1974 | Keating | |
| 3,835,992 A | 9/1974 | Adams, IV | |
| 4,735,342 A | 4/1988 | Goldstein | |
| 4,993,586 A | 2/1991 | Taulbee et al. | |
| 5,133,477 A | 7/1992 | Etheredge et al. | |
| 5,215,236 A | 6/1993 | Waddell | |
| 5,271,522 A | 12/1993 | Ko et al. | |
| 5,299,712 A | 4/1994 | Carlson et al. | |
| 5,358,140 A | 10/1994 | Pellegrino | |
| 5,477,761 A | 12/1995 | Holtsch | |
| 5,511,689 A | 4/1996 | Frank | |
| 5,685,833 A | 11/1997 | Turngren | |
| 5,782,786 A | 7/1998 | Tomaiuolo | |
| 5,843,011 A | 12/1998 | Lucas | |
| 5,891,078 A | 4/1999 | Turngren et al. | |
| 5,961,066 A | 10/1999 | Hambleton | |
| 5,964,375 A | 10/1999 | Carlson et al. | |
| 6,140,549 A | 10/2000 | Pompei, Jr. | |
| 6,213,343 B1 | 4/2001 | Damikolas | |
| 6,299,018 B1 | 10/2001 | Kimbrell | |
| 6,362,388 B1 | 3/2002 | Lucas | |
| 6,755,321 B2 | 6/2004 | Solovay et al. | |
| 6,756,519 B2 | 6/2004 | Johnson et al. | |
| 6,923,320 B2 | 8/2005 | Grossman | |
| 7,240,876 B2 | 7/2007 | Doubleday et al. | |
| 7,506,760 B2 | 3/2009 | Grossman | |
| 7,683,235 B2 | 3/2010 | Wendorf | |
| 7,694,816 B2 | 4/2010 | Kilbey et al. | |
| D637,299 S | 5/2011 | Cowles | |
| 2002/0170918 A1 | 11/2002 | Solovay et al. | |
| 2003/0047566 A1 | 3/2003 | DeVita | |
| 2004/0228990 A1 | 11/2004 | Hines | |
| 2009/0039100 A1 | 2/2009 | King | |
| 2010/0270203 A1 | 10/2010 | Khan | |
| 2010/0276323 A1 | 11/2010 | Grossman | |

OTHER PUBLICATIONS

International Search Report and Written Opinion, PCT/US12/37982, dated Sep. 14, 2012.
"Lifeline 34 Piece Mini Wrist/Pocket First Aid Kit," Safety Central website.

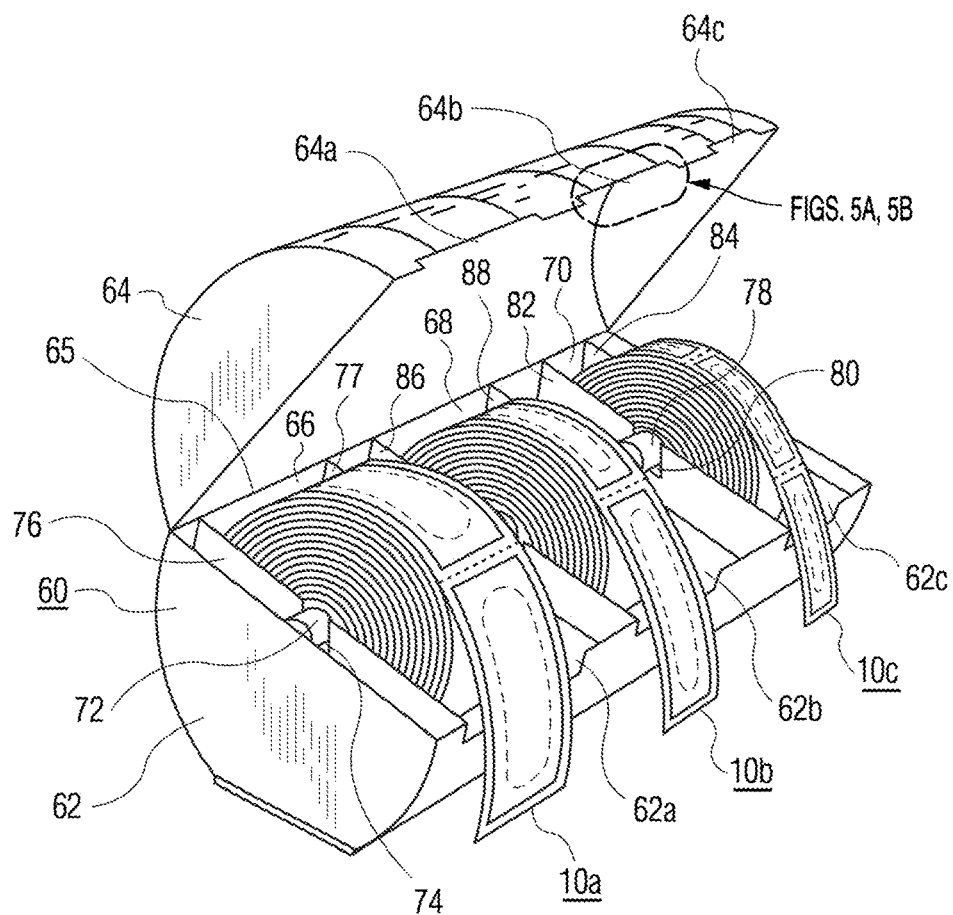
FIG. 5
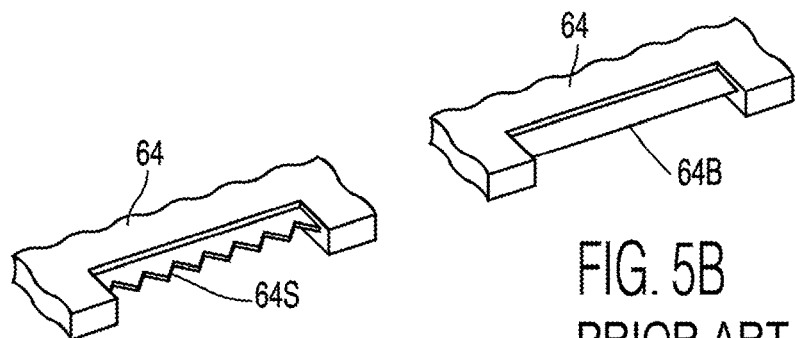
FIG. 5A
PRIOR ART
FIG. 5B
PRIOR ART

ADHESIVE BANDAGE DISPENSING ARRANGEMENTS

BACKGROUND OF THE INVENTION

Field of the Invention

The present invention relates generally to adhesive bandages and, more particularly, to arrangements that facilitate dispensing adhesive bandages to a user.

Description of Related Art

One ubiquitous type of adhesive bandage includes a strip of material, typically plastic or cloth, with an adhesive on one side. A gauze pad is disposed on the same side as the adhesive, and a release liner covers the adhesive side of the strip material and the gauze pad. The entire bandage is enclosed in a package that maintains sterility until it is opened by the user. The bandage is then applied by removing the release liner, positioning the gauze pad over a wound, and adhering the adhesive side of the strip to the skin. Familiar examples of this type of pre-packaged adhesive bandage are sold by Johnson & Johnson as Band-Aid® adhesive bandages and Tyco Healthcare Group as Curity® adhesive bandages.

By their nature, that is, because they are individually pre-packaged, these types of adhesive bandages are available only in predetermined sizes. As a result, these pre-packaged bandages are only sold loose in boxes. This is acceptable for a great many uses, but in some circumstances it can be inconvenient to access a bandage when one is needed. The prior art includes many alternative bandage packaging/dispensing systems and devices, some typical examples being shown in the following references:

| |
|---|
| U.S. Pat. No. 3,530,494 |
| U.S. Pat. No. 4,735,342 |
| U.S. Pat. No. 4,993,586 |
| U.S. Pat. No. 5,133,477 |
| U.S. Pat. No. 5,271,522 |
| U.S. Pat. No. 5,358,140 |
| U.S. Pat. No. 5,477,761 |
| U.S. Pat. No. 5,511,689 |
| U.S. Pat. No. 5,782,786 |
| U.S. Pat. No. 6,213,343 |
| U.S. Pat. No. 6,299,018 |
| U.S. Pat. No. 7,240,876 |
| U.S. Pat. No. 7,694,816 |
| U.S. Pub. No. 2009/0039100 |

Many of these patents eliminate the package enclosing the adhesive bandage and adhere it directly to an elongated release liner strip. The release liner with the bandages secured to it is then wound into a roll or accordion-folded, and the bandages are dispensed by incrementally feeding the strip. This type of dispensing system is shown in U.S. Pat. No. 3,350,494, U.S. Pat. No. 4,993,586, U.S. Pat. No. 5,133,477, U.S. Pat. No. 5,271,522, U.S. Pat. No. 5,358,140, U.S. Pat. No. 5,511,689, U.S. Pat. No. 6,213,343, and U.S. Pat. No. 6,299,018. A variation in which individual bandages are attached end to end to form a strip that is wound into a roll is shown in U.S. Pat. No. 4,735,342 and U.S. Pat. No. 5,782,786. While some users may deem these arrangements more convenient to use than a box of loose bandages, they all require specially manufacturing the bandage roll or strip, which adds to their cost. U.S. Patent Pub. No. 2009/0039100 discloses a device that dispenses individual adhesive bandages one at a time from a stack within the device. The bandages are not packaged and this system appears to pose a risk of compromising the sterility of the bandages, and the user must still load the device with loose bandages.

Another shortcoming of existing adhesive bandages of the type discussed above is the property that makes them convenient in many settings in the first place. That is, they are pre-packaged for ease of use, but are thus available only in certain sizes and shapes. However, sometimes a wound will have a size and/or shape that does not lend itself to being dressed by the available sizes of pre-packaged adhesive bandages. There are patents that disclose devices for dispensing from a roll user-determined lengths of medical bandages. Examples are U.S. Pat. No. 7,240,876 and U.S. Pat. No. 7,694,816. However, these devices do not dispense adhesive bandages of the type under consideration here.

SUMMARY OF THE INVENTION

It is an object of the present invention to improve on known adhesive bandage dispensing arrangements in ways that improve the convenience to the user of accessing and applying bandages to wounds.

In accordance with a first aspect of the invention, pre-packaged adhesive bandages are adhered in their packages to a strip of material. The strip of material can be wound around a spool and optionally enclosed in any suitable dispensing device that enables the user to access the packages of bandages and remove them from the strip one at a time. The strip can also be accordion-folded for dispensing the bandages from a dispensing device. Dispensing devices can be hand-held, wrist-mounted, or configured for placement on a counter top or other surface for ease of access. A dispensing device may include multiple strips of bandages of different sizes.

In another aspect of the invention, a continuous elongate strip (that is, without transverse perforations) has a side with an adhesive substantially covering one side and a gauze pad disposed longitudinally in a median portion of the same side. A release liner covers the side with the adhesive, and the strip can be wound on a spool and optionally disposed in a suitable dispensing device that enables the strip to be withdrawn and severed from the remainder of the roll to form a bandage of any desired length.

According to still another aspect of the invention, a bandage dispensing device can be mounted to a user's wrist to free the user's hands for other tasks and still provide quick access to a supply of bandages. A wrist-mounted dispensing device in accordance with one embodiment of the invention is particularly adapted for use with bandage strips as described and claimed herein.

Thus, one particular aspect of the invention relates to a bandage strip including a plurality of flat adhesive bandage packages, each having sealed therein at least one adhesive bandage comprising a pad and an adhesive substrate for adhering to a patient and holding the pad in place on the patient's skin, and an elongated substrate having at least one row of the packages adhered thereto lengthwise in spaced relation to each other to form a flat, elongated bandage strip. The strip can be configured for dispensing by a user in a number of ways, such as by winding it around a spool for removal of individual bandages from the substrate as the strip is unwound from said spool.

Another particular aspect of the invention relates to a bandage strip including a flat adhesive bandage strip comprising an elongated substrate with at least one continuous strip of absorbent material on one side extending in the elongated dimension of the substrate and an adhesive portion adjacent each outside elongated edge of the substrate, and having a release liner adhered to the adhesive portion and covering said pad, and a spool having the adhesive bandage strip wound lengthwise around said spool.

A device for dispensing adhesive bandages includes a bandage holding compartment for holding a bandage strip including a plurality of flat adhesive bandage packages, each having sealed therein at least one adhesive bandage comprising a pad and an adhesive substrate for adhering to a patient and holding said pad in place on the patient's skin, and an elongated substrate having at least one row of said packages adhered thereto lengthwise in spaced relation to each other to form a flat, elongated bandage strip, and dispensing structure permitting the user to access the bandage strip for withdrawal of at least one flat adhesive bandage package from said compartment. In a specific embodiment, the dispensing device includes at least one strap for attaching the bandage holding compartment to a wrist of the user and the dispensing structure is disposed for enabling the user to extract a bandage from the bandage holding compartment.

BRIEF DESCRIPTION OF THE DRAWINGS

The objects of the invention are not limited by the description herein, and all of the objects and advantages of the invention will be better understood from the detailed description of its preferred embodiments which follows below, when taken in conjunction with the accompanying drawings, in which like numerals and letters refer to like features throughout. The following is a brief identification of the drawing figures used in the accompanying detailed description.

FIG. 5, which includes FIGS. 5A and 5B, is a perspective view of a first embodiment of a dispensing device in accordance with the invention that can be used to dispense different size bandages from multiple bandage strips, with FIGS. 5A and 5B depicting alternate embodiments of a cutting device for severing bandage strips withdrawn from a dispenser.

One skilled in the art will readily understand that the drawings are not strictly to scale, but nevertheless will find them sufficient, when taken with the detailed descriptions of preferred embodiments that follow, to make and use the present invention.

DETAILED DESCRIPTION OF PREFERRED EMBODIMENTS

Figure 1:
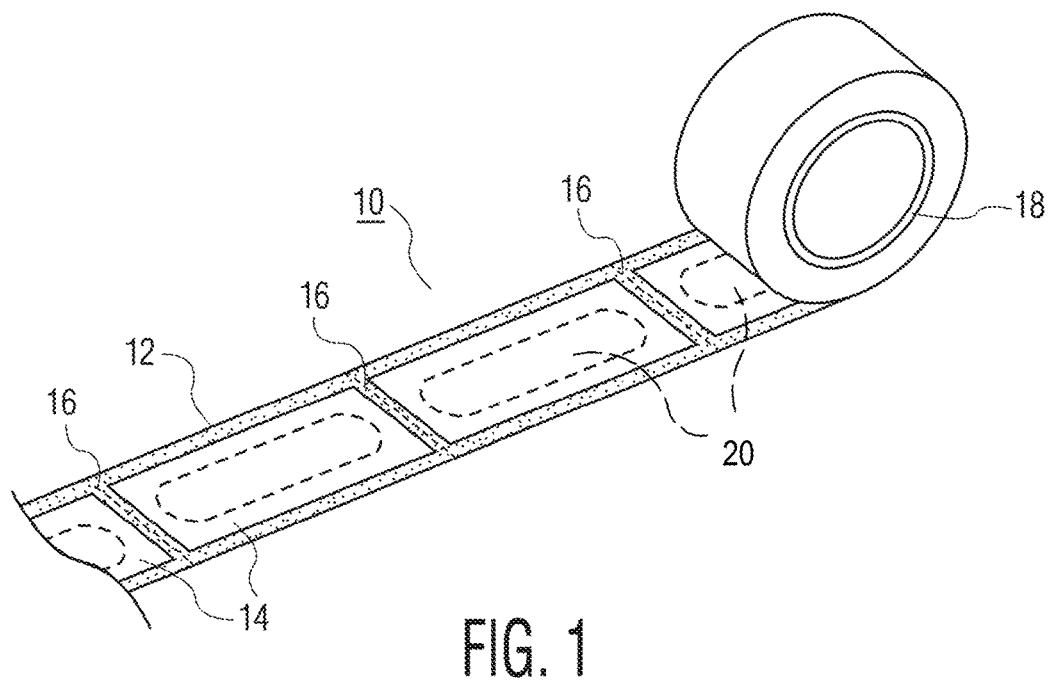
FIG. 1 is a perspective view of a first embodiment of an elongated bandage strip in accordance with the invention, in which pre-packaged adhesive bandages are adhered to an elongated substrate wound on a spool for dispensing.
Figure 2:
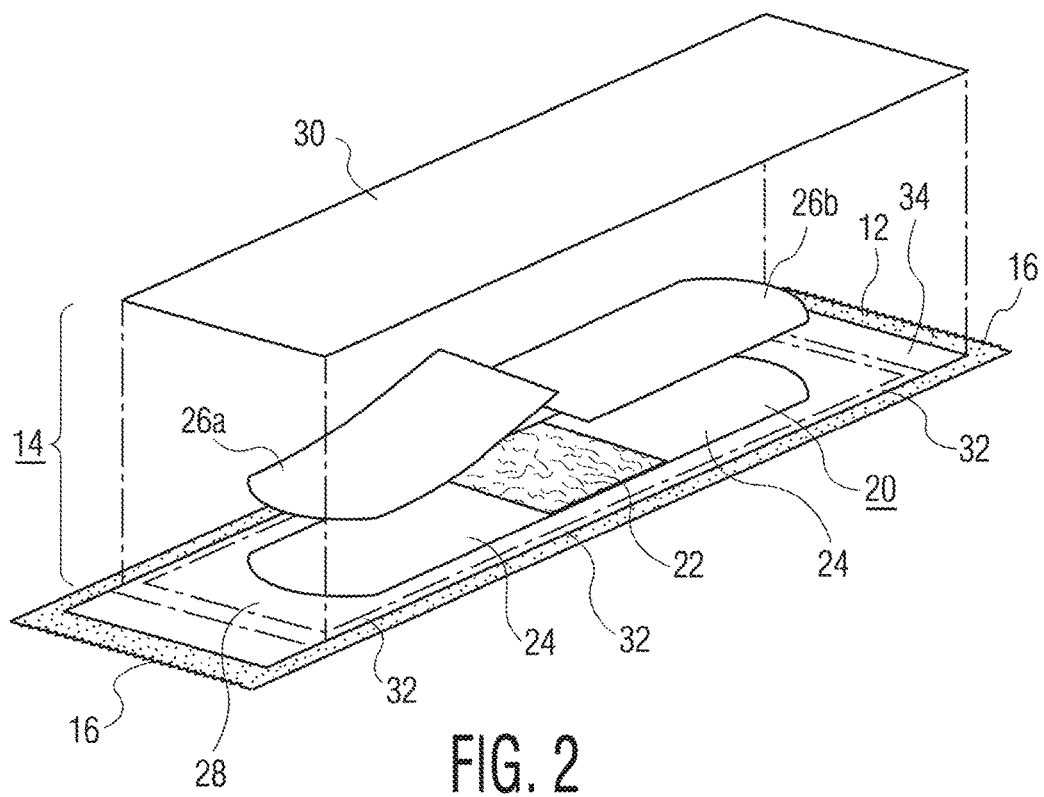
FIG. 2 depicts a single-bandage portion of the elongated substrate of FIG. 1 that has been separated from the strip at perforations in the elongated strip, and shows the adhesive bandage in an exploded view to depict its packaging.

FIGS. 1 and 2 show an elongated bandage strip in accordance with a first embodiment of the invention. In this embodiment an elongated bandage strip 10 includes an elongated substrate 12 coated with an adhesive to which conventional sealed packages 14 of adhesive bandages are disposed in a single row in end-to-end relation. More details of the bandage packages are shown in FIG. 2, discussed further below. Typically, the sealed packages 14 are identical, and in the present embodiment are disposed on the substrate 12 with spaces therebetween. In each space between two packages 14 the substrate has perforations 16 extending transversely across the width of the substrate. The perforations 16 facilitate separation of a length of the substrate with the desired number of individual bandages 14 adhered thereto. It will be appreciated that the perforations are optional and in an alternate arrangement portions of the substrate containing one or more individual bandage packages can be separated from the substrate by other means, such as a serrated cutting edge or sliding blade of a dispensing device or a scissors.

In the depicted embodiment, the elongated bandage strip 10 comprising the substrate 12 and the bandage packages 14 is wound on a spool 18, from which a desired length of the strip can be unwound, as shown in FIG. 1. The spool 18 may be manipulated by a user to unwind a desired length of the strip 10, or it can be disposed in one or more known dispensing devices such as those shown in patents referred to above. In other variations, the elongated strip can be made wide enough to accommodate multiple rows of bandage packages disposed in side-by-side relation. In addition, the substrate 14 can be perforated lengthwise between the side-by-side rows of packages to facilitate removal of bandage packages as discussed above. It will also be appreciated that the invention is not limited to using any particular adhesive bandage configuration. For example, most adhesive bandage suppliers make packaged bandages in many shapes, such as small and large squares, shapes adapted to be applied to the end of a finger, and others. Any pre-packaged, self-contained adhesive bandage can be used in this embodiment without departing from the spirit and scope of the invention.

FIG. 2 shows a detail of the conventional adhesive bandage package 14 removably adhered to the substrate 12 in accordance with the present embodiment of the invention. FIG. 2 shows a portion of the substrate 12 that has been removed from the remainder of the substrate 12 at the perforations 16. (It will be appreciated from the discussion above that a portion of the substrate 12 holding a single bandage package 14 is shown in FIG. 2 solely for illustrative purposes and that more than one bandage package 14 at a time can be removed from the strip 10 if desired.) Each bandage package 14 has sealed therein a sterile adhesive bandage 20 of conventional design, with a pad 22 of absorbent material such as gauze on an adhesive substrate 24. As is well known, the pad 22 in use is placed on the user's skin (typically over a wound or other place on a user requiring it to be covered for medical reasons) and held in place by the adhesive substrate 24. Such substrates are typically plastic, cloth, or other material that has sufficient strength and flexibility to hold the pad 22 in place as the user moves.

In the conventional fashion, the adhesive side of the substrate 24 is covered by a two-part release layer 26a and 26b that is coextensive with the adhesive substrate 24. The two parts overlap at the pad 22 and can be peeled away by the user for application of the bandage 20. Sterility of the bandage 20 is maintained by a wrapper that in most commercial configurations comprises a lower sheet of paper 28 and an upper sheet of paper 30 that are tightly sealed at their peripheries 32. At one end a flap 34 that is left unsealed can be grasped by the user to peel the upper sheet 30 from the lower sheet 28 to permit access to the adhesive bandage 20. (In describing embodiments of the invention, terms indicating direction or orientation, such as "lower," "upper," "front," "rear," etc., may be used to facilitate the description. They do not imply that the invention is limited to a particular orientation of the structure being described.)

In this embodiment of the invention the lower sheet 28 of the bandage package 14 is removably adhered to the substrate 12 to form the flat, elongated, bandage strip 10. The strip 10 is wound on the spool 18 for convenience in accessing the desired number of adhesive bandages. Those skilled in the art will appreciate that any adhesive can be used that will hold the bandage package in place while permitting the strip to be wound onto the spool, and at the same time permitting the user to readily remove the bandage package from the substrate 12 when desired. In one implementation of the invention, the lower sheet 28 of the bandage package can be adhered to the substrate 12 at discrete spots rather than over the entire surface of the lower layer. In another variation, the package can be more firmly adhered to the substrate 12, enabling the bandage to be dispensed from the package by peeling the top sheet 30 from the bottom sheet 28, while the latter remains adhered in place on the substrate.

By using conventional, sealed packages of adhesive bandages, the elongated bandage strip 10 is considerably less expensive to manufacture than the strips of adhesive bandages according to the prior art discussed above. In addition, the sterility of the adhesive bandages as guaranteed by the original manufacturer of the packaged bandages is not disturbed, which means that any government and/or industry requirements regarding sterility of the individual bandages remain satisfied because the integrity of the packages is not compromised by adhering them to the substrate 12. In addition, a bandage strip in accordance with this embodiment can be used in many different dispensing devices, some of which are discussed further below.

Figure 3:
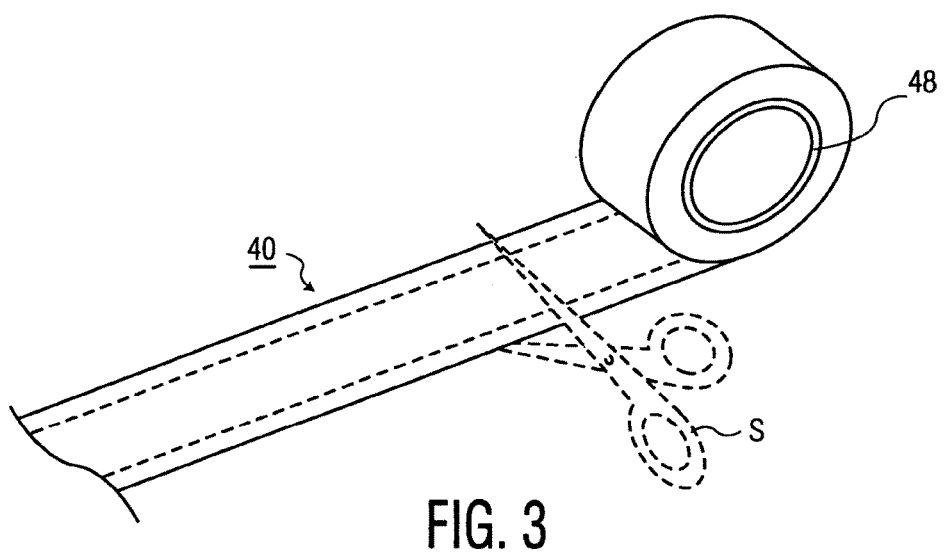
FIG. 3 is a perspective view of a second embodiment of an elongated bandage strip in accordance with the invention, in which a continuous bandage is wound on a spool for dispensing.
Figure 4:
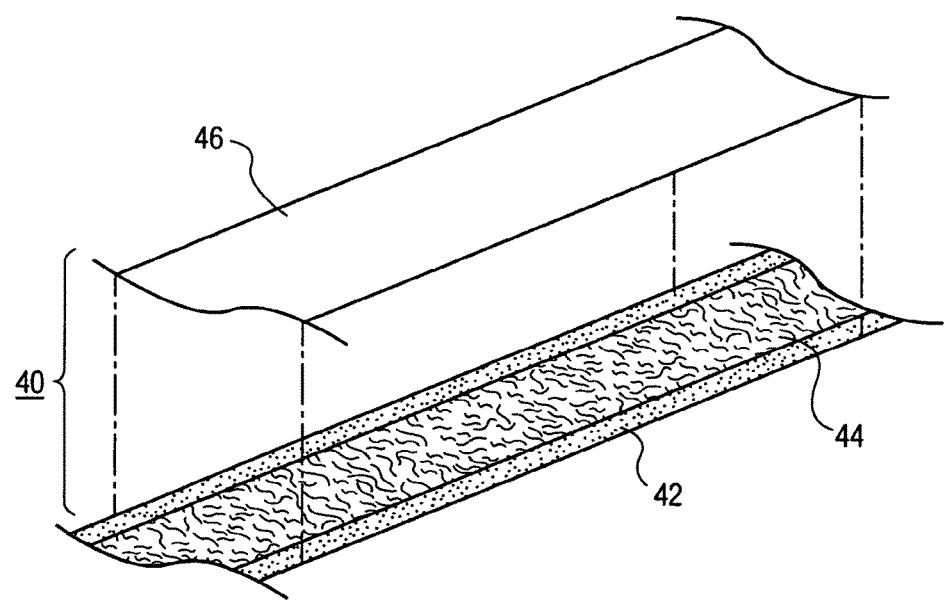
FIG. 4 is an exploded view of a portion of the strip in FIG. 3.

FIGS. 3 and 4 depict an elongated bandage strip in accordance with a second embodiment of the invention. As seen best in the exploded view of FIG. 4, an elongated bandage strip 40 comprises a continuous substrate 42 coated with an adhesive to which a continuous gauze strip 44 is adhered. A release liner 46 covers the substrate 42 and is coextensive with it in a direction transverse to the longitudinal direction of the strip 40. Thus, the release liner 46 protects the gauze strip 44 from contamination.

In a fashion similar to the first embodiment described above, the elongated bandage strip 40 comprising the substrate 42 and the release liner 46 is wound on a spool 48, from which a desired length of the strip can be unwound, as shown in FIG. 3. Typically, the gauze strip 44 extends in one piece for the entire length of the strip 40 wound on the spool 48. The spool may be manipulated by a user to unwind a desired length of the strip 44, which can then be cut into desired lengths using a scissors S (not depicted to scale). As with a bandage strip in accordance with the first embodiment discussed above, the spool 48 can also be disposed in many different types of dispensing devices, such as those shown in many of the patents referred to above or those discussed below.

One of the features of bandage strips according to the present invention is their ability to be used with many prior art dispensing devices disclosed in the patents enumerated above. The descriptions of dispensing devices shown in those patents are hereby incorporated by reference as if set in full herein. It will be clear to one skilled in the art how bandage strips in accordance with the present invention can be used with any of those dispensing devices.

As an example, FIG. 5 depicts the bandage strip dispenser disclosed in U.S. Pat. No. 4,735,342, which has been incorporated herein by reference, used with bandage strips in accordance with the embodiment of the invention discussed above in connection with FIGS. 1 and 2. The dispensing device includes a case 60 with a lower receptacle portion 62 having a cover 64 connected to the receptacle portion at a hinge 65 at the rear of the case. The receptacle portion 62 has a flat bottom for resting the device on a counter top or other surface, and three internal compartments 66, 68, and 70 sized to receive bandage strips 10a, 10b, and 10c. The bandage strips correspond in structure to the bandage strip 10 shown in FIGS. 1 and 2, except that they are different widths in a direction traverse to their length. The strips 10a, 10b, and 10c are each wound on a respective spool. The strip 10a is wound on a spool having an axle 72 with one end resting in a slot 74 in one wall 76 of the compartment 66 and another end (not shown) resting in a slot (not shown) in the other wall 77 of the compartment 66. The strip 10c is wound on a spool with an axle 78 resting in a slot 80 in one wall 82 of the compartment 70 and another end resting in a slot (not shown) in the other wall 84 of the compartment 70. The strip 10b is similarly wound on a roll with an axle (not shown) having ends mounted in walls 86 and 88 of the compartment 68 in the same manner.

In use, the cover 64 is closed and latched in any suitable manner to the receptacle portion 62. Cutouts 64a, 64b, and 64c in the cover 64 and cooperating cutouts 62a, 62b, and 62c in the receptacle portion 62 form slots at the front of the dispenser through which a user can extract the bandage strips 10a, 10b, and 10c. As the user pulls out a bandage strip, individual bandage packages are presented to the user. Portions of the strips can be removed at the perforations 16. Alternatively, if the strips are not perforated each slot can be provided with a serrated edge 64S (FIG. 5A) or a cutting blade 64B (FIG. 5B) to cut through the strip and sever it between individual bandages. Another example of such a cutting device is shown in U.S. Pat. No. 5,477,761, which has been incorporated herein by reference. When all of the bandages on a strip have been used, the empty spool can be replaced with a full spool by opening the cover 64 at the hinge 65 and dropping it in place.

In addition, the dispensing device shown in FIG. 5 is not limited to use just with different size adhesive bandages of the configuration shown in FIG. 2. It can also be used with bandage strips having packages with different configurations of adhesive bandages, as discussed above. Moreover, multiple bandage strips of different widths, with the configuration shown in FIGS. 3 and 4, can also be used with the dispensing device shown in FIG. 5, particularly one with a cutting device having a blade with which the user can sever a portion of the strip having a desired length. Such bandage strips can also be used with other dispensing devices and arrangements in the U.S. patents incorporated herein by reference. In another variation, the case 60 may be configured for mounting on a belt or other article of clothing of a user for quick and convenient access.

Figure 6:
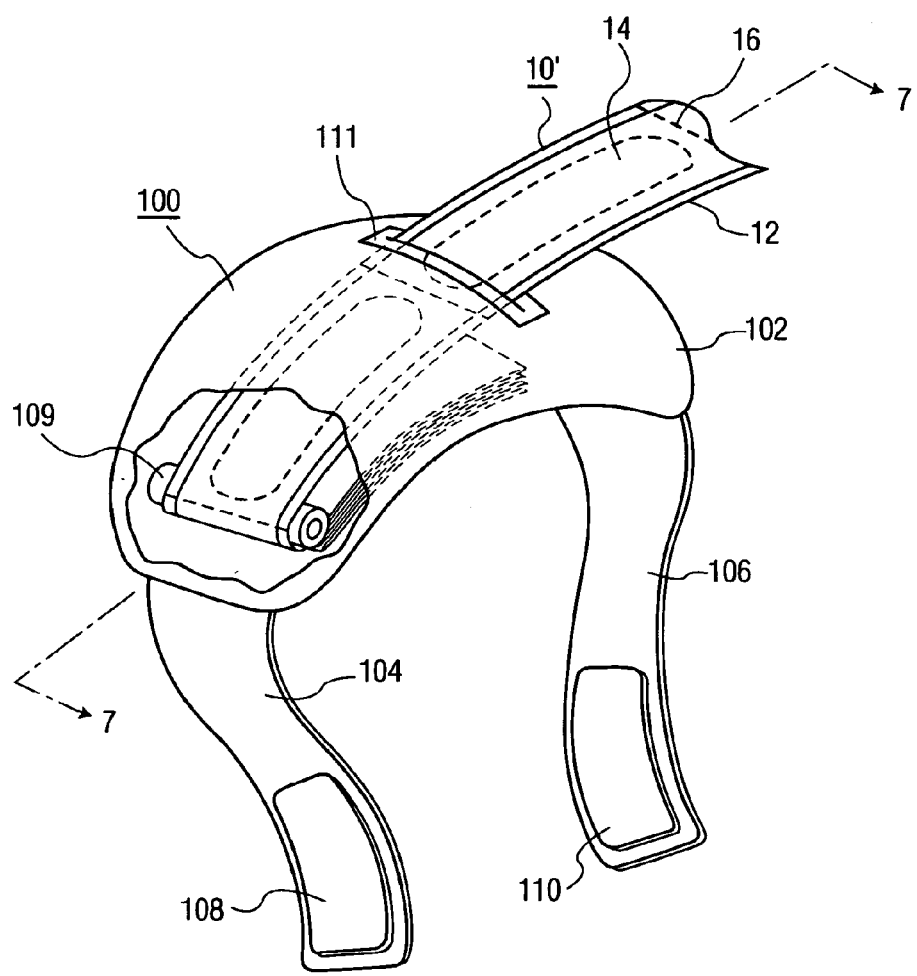
FIG. 6 is a perspective view of a second embodiment of a dispensing device in accordance with the invention that can be mounted to a user's wrist for dispensing bandages from a bandage strip.
Figure 7:
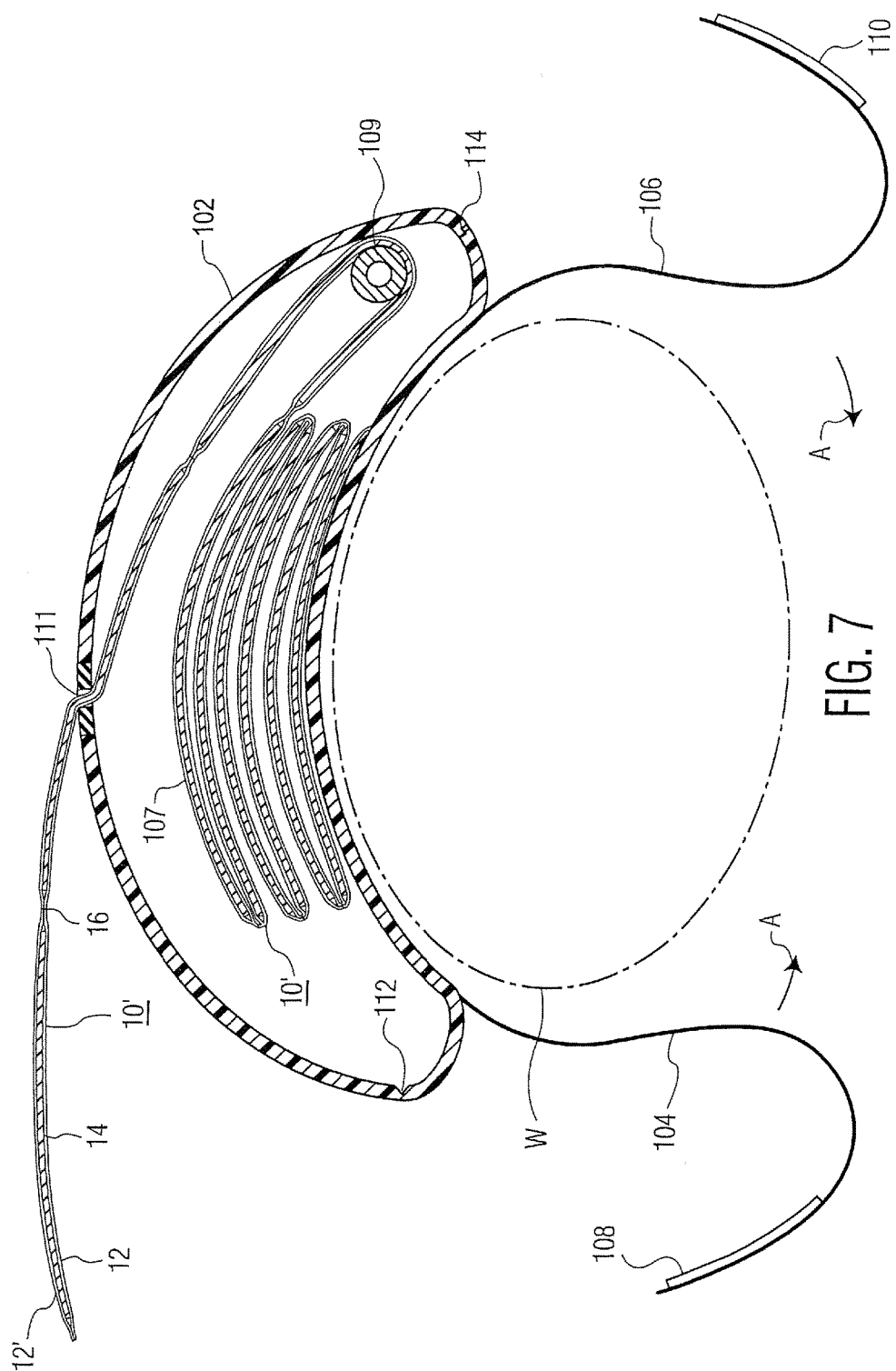
FIG. 7 is a cross-section of the dispensing device in FIG. 6 taken along the line 7-7 in FIG. 6.

In addition to being capable of use with many prior art dispensing devices, bandage strips in accordance with the present invention are also particularly adapted for use with a wrist-mounted dispensing device 100 shown in FIGS. 6 and 7. The dispensing device 100 is shown with a bandage strip 10 like that shown in FIGS. 1 and 2, slightly modified and accordion-folded into a housing 102, as described in more detail just below. The housing 102 includes straps 104 and 106 with Velcro® strips 108 and 110 at their ends. The housing 102 is preferably molded of a suitable plastic material in a contoured shape that will match the wrist W of a user (see FIG. 7), and the straps 104 and 106 are wrapped around the user's wrist as indicated by the arrows A to bring the Velcro® strips 108 and 110 into contact with each other and hold the dispensing device 100 in place on the user's wrist. It will be clear, of course, that other ways of securing the device to the user's wrist, such as a buckle-type arrangement, could also be used.

Referring to FIG. 7, the housing 102 is seen in cross-section. It accommodates a bandage strip 10' that is identical to the bandage strip 10 in FIGS. 1 and 2, except that it includes a top release liner 12', for a purpose to be described. (The top release liner is omitted from FIG. 6 for clarity.) The bandage strip 10' is accordion-folded into a stack 107 inside the housing 102, and the end is fed over a guide roller 109 and through a dispensing slot 111 to the outside of the housing 102. The top release liner 12' prevents the adhesive top surface of the substrate 12 from adhering to an abutting top surface of the substrate when the strip 10' is folded into the stack 107. However, in an alternate construction, the bandage packages 14 can be adhered to the substrate 12 by applying adhesive only to portions of the substrate that are covered by the packages 14, as discussed above in connection with FIG. 1, which would permit the top release liner 12' to be omitted. However, it is believed that covering the packages 14 with the top release liner 12' adhered to the substrate 12 will help keep the packages 14 in place on the substrate 12 as the substrate 12 is drawn around the roller 109 and through the slot 111.

As seen in the cross sectional view of the strip 10' in FIG. 7, the substrate 12 and the release liner 12' both include perforations 16. A portion of the periphery of the housing 102 has a notch 112 molded into it to form a hinge, and the remainder of the periphery is divided to permit a top part of the housing to be rotated about the hinge to an open position to provide access to the inside of the housing. The edges of the divided portion have cooperating shoulders 114 that frictionally engage each other to hold the top part closed.

In use, the dispensing device 100 is secured to one wrist W of the user as discussed above. The user pulls the bandage strip 10' from the slot 111 with his or her other hand, and separates a portion of the strip 1Q containing an individual packaged bandage package 14 at the perforations 16. The slot 111 is sufficiently narrow to hold the strip 10' in place through friction and permit the user to tear away the needed length of the strip 10'. When the entire bandage strip 10' has been consumed, the user can open the top part of the housing 102 about the hinge 112 and insert a fresh bandage strip 10'. The top portion is then rotated back into place and the shoulders 114 hold it in place. To more positively hold the top part in place, the shoulders can include one or more beads in a surface of one shoulder that fit into one or more corresponding depressions in the facing surface of the other shoulder. In that case, the housing is molded so that the user will sense a positive "click" when the beads are properly in place in the depressions. Of course, other latching arrangements are possible and the invention is not limited to any particular such arrangement.

Other variations in the construction and operation of the wrist-mounted dispensing device 100 are likewise possible. For example, dispensing guides may be molded into the interior of the housing to aid in positioning the strip 10' for smooth dispensing through the slot 111. In addition, the device may be configured to permit the user to pull out a length of the bandage strip and sever it using a serrated edge on the device. Or the device can incorporate a cutting blade, as discussed above in connection with FIG. 5. The dispenser may also be formed to accommodate a bandage strip on a spool like one of those shown in FIG. 5 instead of accordion folding the strip. It will also be appreciated that a wrist-mounted dispenser in accordance with this aspect of the invention is not limited to use with bandage strips like those described above in connection with FIGS. 1-4. It can also be used with loose, prepackaged bandages (such as the adhesive bandage package 14 shown in FIG. 2) and bandage strips shown in many of the above-mentioned patents, such as U.S. Pat. No. 3,530,494, No. 4,735,342, No. 4,993,586, No. 5,113,477, No. 5,358,140, No. 5,511,689, No. 5,782, 786, No. 6,213,343, No. 6,299,018, and U.S. Pub. No. 2009/0039100.

Those skilled in the art will readily recognize that only selected preferred embodiments of the invention have been depicted and described, and it will be understood that various changes and modifications can be made other than those specifically mentioned above without departing from the spirit and scope of the invention, which is defined solely by the claims that follow.

What is claimed is:

1. In combination, adhesive bandages and a dispenser for dispensing the adhesive bandages, the combination comprising:

an elongated bandage strip comprising an elongated substrate carrying a plurality of adhesive bandage packages, each bandage package including two sheets adhered to each other at mutually facing peripheral portions providing a sealed enclosure containing at least one flat adhesive bandage, said adhesive bandage comprising a bandage substrate with an adhesive side for adhering to a patient and holding the bandage in place on a patient's skin and a release layer covering the adhesive side of the bandage substrate, wherein the release layer is adhered only to the adhesive side of the bandage substrate to permit separation of the sheets and removal of the adhesive bandage from the enclosure of the two sheets with the entire release layer remaining in place on the bandage substrate, the elongated substrate having at least one row of the bandage packages arranged adjacently along the elongated substrate with one of the sheets adhered to a surface of the elongated substrate to form the elongated bandage strip with adjacent bandage packages having a space therebetween; and a dispenser holding the elongated bandage strip and providing access thereto for permitting withdrawal from the dispenser of a length of the elongated bandage strip sufficient to permit removal of at least one of the adhesive bandages from the elongated substrate by separating the sheets, with the one sheet of the bandage package adhered to the elongated substrate remaining on the elongated substrate when the sheets are separated, wherein:

the dispenser comprises a housing containing the elongated bandage strip, the housing having an opening through which the elongated bandage strip can be withdrawn, the elongated substrate having perforations extending transversely thereacross in the spaces between adjacent bandage packages for permitting the length of the elongated bandage strip withdrawn from the housing to be separated from the elongated bandage strip remaining in the housing by tearing it at the perforations, the surface of the elongated substrate is substantially covered by an adhesive to which the bandage packages are adhered, and the bandage packages are narrower than the elongated substrate to provide an adhesive-covered periphery surrounding each bandage package, the elongated bandage strip further includes a release liner adhered to the adhesive-covered periphery surrounding each bandage package, the release liner having perforations in substantially the same locations as the perforations of the elongated substrate, and the elongated bandage strip is arranged in the housing as a roll with adjacent bandage packages extending circumferentially along the roll.

2. The combination as in claim 1, wherein the dispenser includes attaching structure for attaching the housing to a user in a position permitting the user to reach the opening and withdraw the elongated bandage strip.

3. The combination as in claim 1, wherein the dispenser includes a plurality of bandage holding compartments, each compartment having therein a respective elongated bandage strip roll and an opening through which the elongated substrate of the roll in the compartment can be withdrawn.

4. The combination as in claim 3, wherein each elongated bandage strip roll is wound on a respective spool.

5. The combination as in claim 3, wherein the elongated substrate has only one row of the bandage packages thereon.

6. The combination as in claim 1, wherein the elongated substrate has only one row of the bandage packages thereon.

7. In combination, adhesive bandages and a dispenser for dispensing the adhesive bandages, the combination comprising:

an elongated bandage strip comprising an elongated substrate carrying a plurality of adhesive bandage packages, each bandage package including two sheets adhered to each other at mutually facing peripheral portions providing a sealed enclosure containing at least one flat adhesive bandage, said adhesive bandage comprising a bandage substrate with an adhesive side for adhering to a patient and holding the bandage in place on a patient's skin and a release layer covering the adhesive side of the bandage substrate, wherein the release layer is adhered only to the adhesive side of the bandage substrate to permit separation of the sheets and removal of the adhesive bandage from the enclosure of the two sheets with the entire release layer remaining in place on the bandage substrate, the elongated substrate having at least one row of the bandage packages arranged adjacently along the elongated substrate with one of the sheets adhered to a surface of the elongated substrate to form the elongated bandage strip with adjacent bandage packages having a space therebetween; and a dispenser holding the elongated bandage strip and providing access thereto for permitting withdrawal from the dispenser of a length of the elongated bandage strip sufficient to permit removal of at least one of the adhesive bandages from the elongated substrate by separating the sheets, with the one sheet of the bandage package adhered to the elongated substrate remaining on the elongated substrate when the sheets are separated, wherein:

the dispenser comprises a housing containing the elongated bandage strip, the housing having an opening through which the elongated bandage strip can be withdrawn, the opening has a cutting device for permitting the length of the elongated bandage strip withdrawn from the housing to be separated from the elongated bandage strip remaining in the housing by severing the elongated bandage strip in the space between adjacent bandage packages, the surface of the elongated substrate is substantially covered by an adhesive to which the bandage packages are adhered, and the bandage packages are narrower than the elongated substrate to provide an adhesive-covered periphery surrounding each bandage package, the elongated bandage strip further includes a release liner adhered to the adhesive-covered periphery surrounding each bandage package, and the elongated bandage strip is arranged in the housing as a roll with adjacent bandage packages extending circumferentially along the roll.

8. The combination as in claim 7, wherein the dispenser includes attaching structure for attaching the housing to a user in a position permitting the user to reach the opening and withdraw the elongated bandage strip.

9. The combination as in claim 7, wherein the dispenser includes a plurality of bandage holding compartments, each compartment having therein a respective elongated bandage strip roll and an opening through which the elongated substrate of the roll in the compartment can be withdrawn.

10. The combination as in claim 9, wherein each elongated bandage strip roll is wound on a respective spool.

11. The combination as in claim 9, wherein the elongated substrate has only one row of the bandage packages thereon.

12. The combination as in claim 7, wherein the cutting device includes a serrated edge at the opening.

13. The combination as in claim 7, wherein the cutting device includes a cutting blade at the opening.

14. The combination as in claim 7, wherein the elongated substrate has only one row of the bandage packages thereon.

\* \* \* \* \*